(12) United States Patent
Bouneff

(10) Patent No.: US 7,874,839 B2
(45) Date of Patent: Jan. 25, 2011

(54) POWERED SURGICAL INSTRUMENTS

(75) Inventor: Anthony B. Bouneff, Gaston, OR (US)

(73) Assignee: WestPort Medical, Inc., Salem, OR (US)

( * ) Notice: Subject to any disclaimer, the term of this patent is extended or adjusted under 35 U.S.C. 154(b) by 0 days.

(21) Appl. No.: 11/707,465

(22) Filed: Feb. 15, 2007

(65) Prior Publication Data
US 2007/0141529 A1 Jun. 21, 2007

Related U.S. Application Data

(63) Continuation-in-part of application No. 10/890,711, filed on Jul. 13, 2004, now abandoned.

(51) Int. Cl.
*A61C 1/07* (2006.01)
(52) U.S. Cl. ...................................... 433/121; 433/118
(58) Field of Classification Search .................. 433/118, 433/119, 120, 121, 122, 123, 124
See application file for complete search history.

(56) References Cited

U.S. PATENT DOCUMENTS

| | | | | |
|---|---|---|---|---|
| 352,456 | A | * | 11/1886 | Foerster ...................... 433/121 |
| 363,911 | A | * | 5/1887 | Register ...................... 433/121 |
| 414,353 | A | * | 11/1889 | Wells ......................... 433/121 |
| 459,891 | A | * | 9/1891 | Scott ........................... 433/120 |
| 557,159 | A | * | 3/1896 | Skinner ...................... 433/118 |
| 1,464,824 | A | * | 8/1923 | Kollock et al. ................. 74/55 |
| 2,100,319 | A | | 11/1937 | Brown et al. |
| 2,129,212 | A | * | 9/1938 | Hollenback ................. 433/100 |
| 2,421,354 | A | | 5/1947 | Reiter ......................... 606/100 |
| 2,542,695 | A | * | 2/1951 | Neff et al. ................... 433/121 |
| 2,831,132 | A | | 4/1958 | Jackson |
| 3,547,006 | A | | 12/1970 | Rudman |
| 3,640,280 | A | | 2/1972 | Slanker et al. |
| 3,898,739 | A | | 8/1975 | Gayso |
| 3,921,044 | A | | 11/1975 | McShirley |

(Continued)

FOREIGN PATENT DOCUMENTS

DE 4209191 5/1993

OTHER PUBLICATIONS

Nobel Biocare Implant Placement Manual, *Replace Select Tapered*, front cover, pp. 2-43 and back cover, 2002.

(Continued)

*Primary Examiner*—Ralph A Lewis
(74) *Attorney, Agent, or Firm*—Kolisch Hartwell, P.C.

(57) ABSTRACT

A powered surgical instrument is provided. In some embodiments, the powered surgical instrument may include a housing; a receiver, at least a portion of the receiver is movably received within the housing, a distal end portion of the receiver being configured to receive an expander adapted to expand a tooth socket within a treatment area, wherein the receiver is configured to move between a first receiver position and a second receiver position; a bias assembly operatively connected to the receiver and configured to urge the receiver towards the second receiver position; and an actuator disposed within the housing and configured to move the receiver at least from the first receiver position to the second receiver position, wherein the receiver is configured to be selectively moved between the first and second receiver positions independent of the actuator.

20 Claims, 8 Drawing Sheets

U.S. PATENT DOCUMENTS

| | | | |
|---|---|---|---|
| 4,219,619 | A | 8/1980 | Zarow |
| 4,608,019 | A | 8/1986 | Kumabe et al. |
| 4,629,426 | A | 12/1986 | Levy |
| 5,145,369 | A | 9/1992 | Lustig et al. |
| 5,151,030 | A | 9/1992 | Comeaux |
| 5,314,333 | A | 5/1994 | Irmer et al. |
| 5,924,864 | A | 7/1999 | Loge et al. |
| 5,951,581 | A | 9/1999 | Saadat et al. |
| 6,312,255 | B1 | 11/2001 | Hudak |
| 6,368,108 | B1 | 4/2002 | Locante et al. |
| 6,409,507 | B1 | 6/2002 | Postal et al. |
| 6,436,107 | B1 | 8/2002 | Wang et al. |
| 6,626,670 | B1 | 9/2003 | Lerner et al. |
| 2003/0003418 | A1 | 1/2003 | Kumabe |
| 2003/0078586 | A1 | 4/2003 | Shapira |
| 2004/0190803 | A1 * | 9/2004 | Deshpande ............ 384/297 |
| 2005/0118550 | A1 | 6/2005 | Turri |
| 2005/0181328 | A1 | 8/2005 | Milne |

OTHER PUBLICATIONS

International Search Report, Jul. 14, 2008, 3 pages, U.S. Patent and Trademark Office.

Written Opinion, Jul. 14, 2008, 7 pages, U.S. Patent and Trademark Office.

The International Bureau of WIPO, International Preliminary Report on Patentability, Aug. 19, 2009, 3 pages.

* cited by examiner

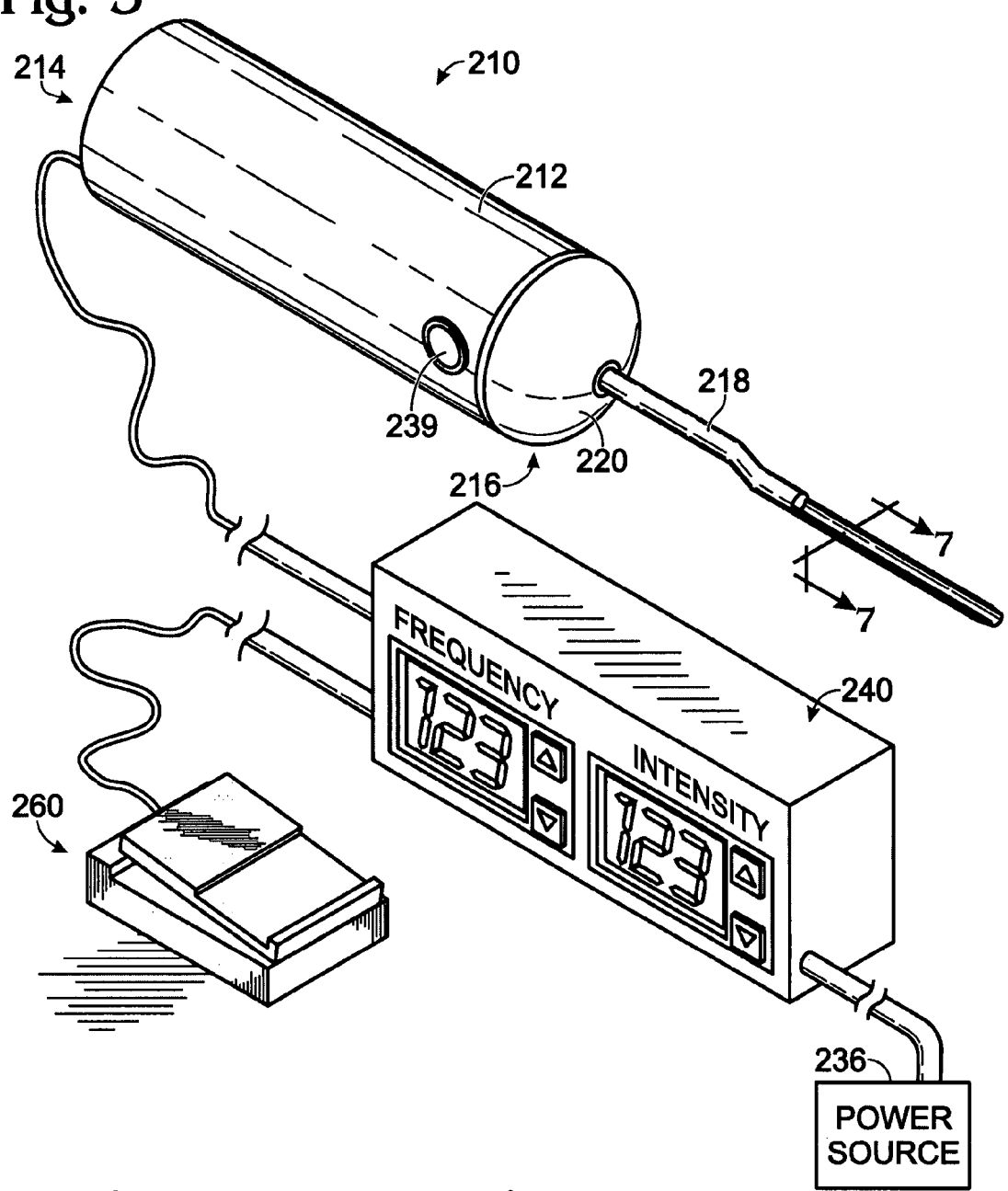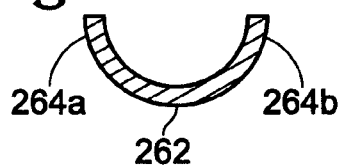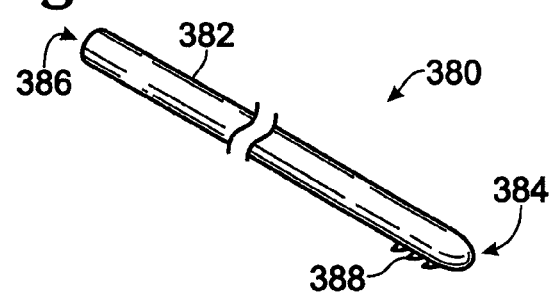

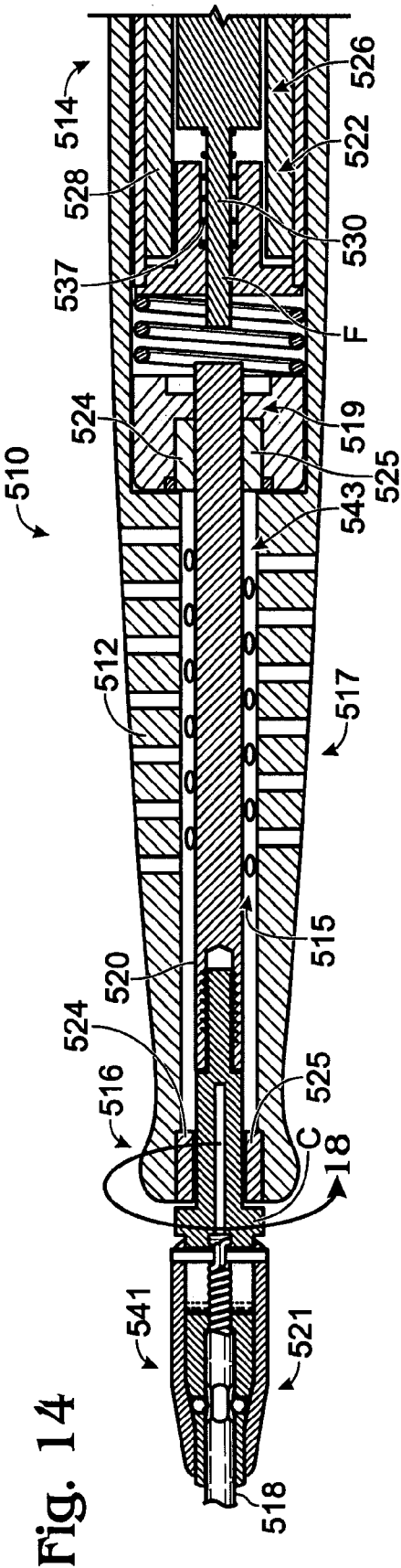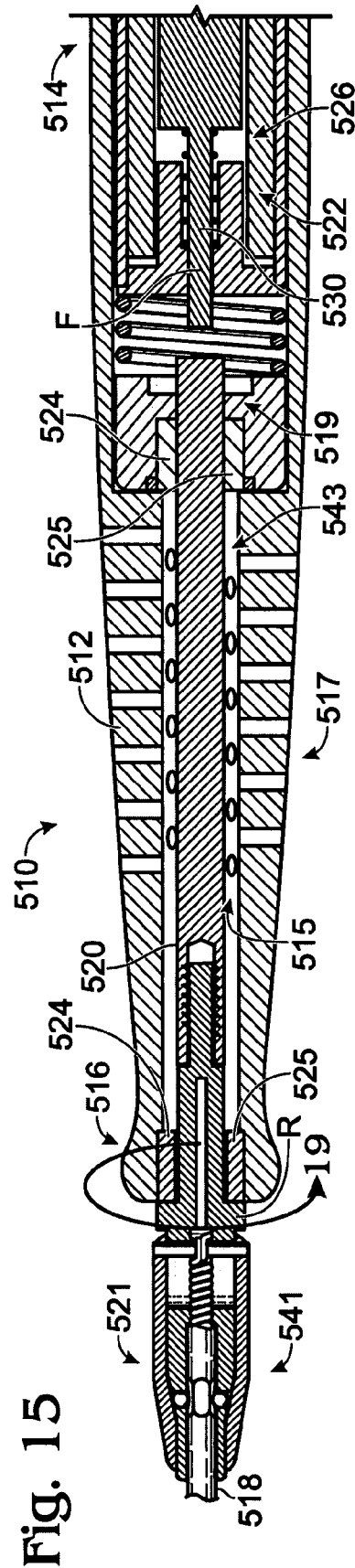

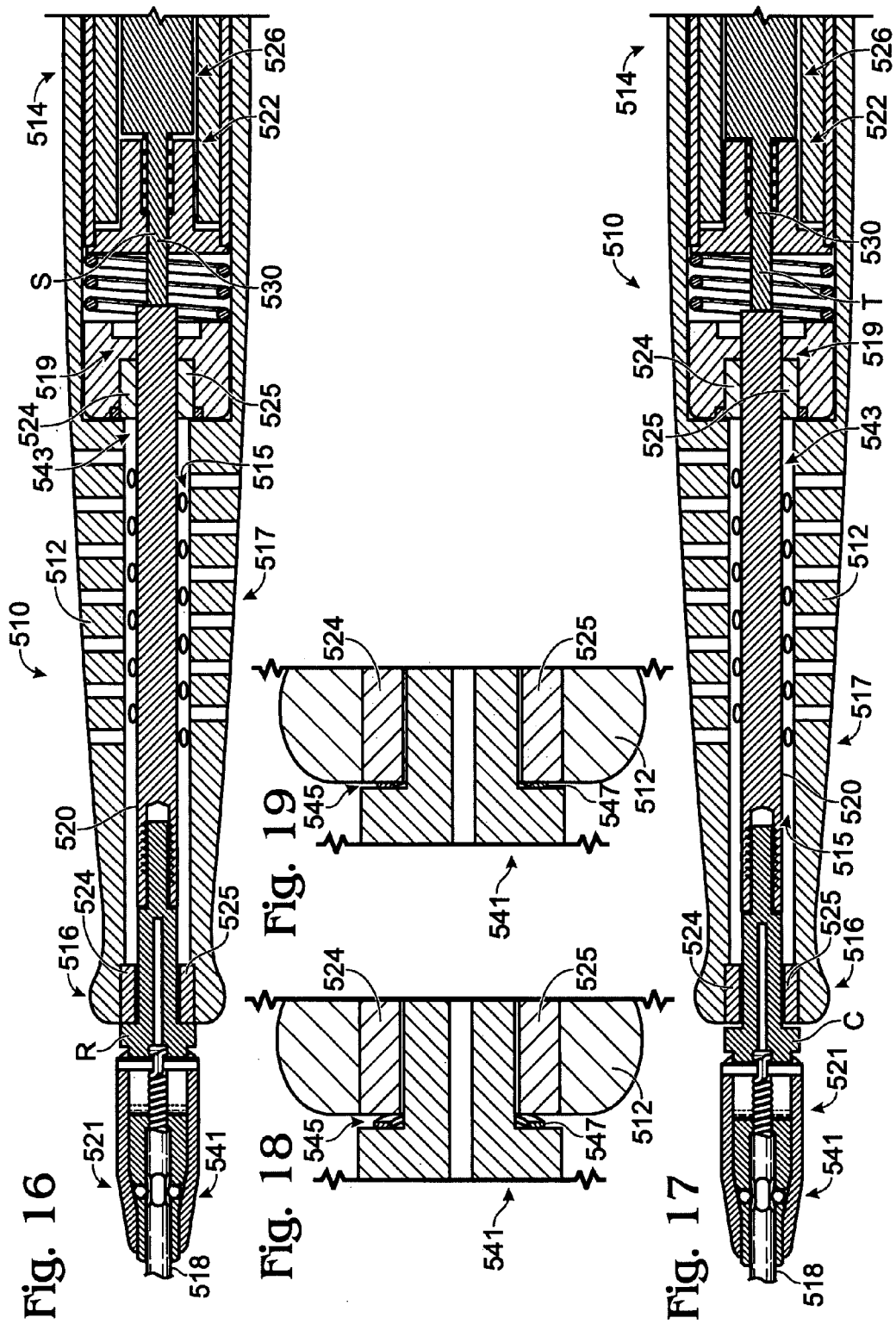

POWERED SURGICAL INSTRUMENTS

CROSS-REFERENCE TO RELATED APPLICATIONS

This application is a continuation-in-part of U.S. patent application Ser. No. 10/890,711, filed Jul. 13, 2004 now abandoned and entitled "Powered Surgical Instrument." The complete disclosure of that application is herein incorporated by reference for all purposes.

BACKGROUND OF DISCLOSURE

A tooth may need to be extracted from the mouth for a variety of reasons. For example, in some situations it may be desirable to extract a tooth that is decayed, damaged or loose. Other times, teeth may be extracted for 'orthodontic' reasons, such as to provide room for other teeth, enable other teeth to grow, etc.

In its most basic form, a tooth includes a crown, which is the upper, visible portion of the tooth, and a root structure, which is hidden from view in the boney substructure of alveolar bone comprising the socket. A tooth is secured in place by a combination of factors, including the structural relationship between the root structure and the alveolar bone of the gums and the periodontal ligaments connecting the tooth root structure to the alveolar bone.

Depending on the type of extraction, removal of a tooth may require the skills of dentists, oral surgeons, or similar professionals. As used herein, such professionals are referred to as dental professionals. The term "dental professional" should be read broadly to include any individual trained or skilled to extract teeth from a human or animal.

When a tooth includes a sufficient amount of sturdy crown to enable a dental professional to grip the tooth, the tooth may be removed by rocking the tooth until it is released from the socket. The rocking motion accomplishes at least two purposes. First, the rocking motion expands the alveolar bone in the region circumscribing the tooth socket. That rocking motion changes the structural relationship between the tooth root structure and the alveolar bone. Prior to rocking the tooth, the root structure and the alveolus are associated such that the alveolar bone provides a substantial amount of the retentive force on the tooth. The rocking motion compresses the alveolar bone surrounding the root structure, expanding the tooth socket away from the root structure.

Additionally, the rocking motion stretches the periodontal ligaments that extend from the root structure to the alveolar bone. The stretching of the ligaments may break some or all of the periodontal ligaments from the bone. In other cases, the periodontal ligaments may be stretched, but still intact, after completing the rocking motion to expand the tooth socket. In those cases, the dental professional may be able to break the tooth free from the ligaments by pulling on the tooth.

While the rocking technique allows a dental professional to remove a tooth, the procedure is not ideal. The procedure typically requires the dental professional to exert a great deal of force on the tooth to compress the alveolar bone. Additionally, the limited space in the mouth in which the dental professional must complete this rocking technique complicates the procedure. Furthermore, in some circumstances, the rocking motion can be applied with too much force damaging the crown of the tooth before the socket is sufficiently expanded or resulting in damage or breaks in the alveolar bone. If the crown is sufficiently damaged, the tooth may need to be treated as a surgical extraction to accomplish the removal. A surgical extraction traditionally required the removal of bone utilizing a rotary instrument or chisel. Further, broken alveolar bone may complicate the installation of a dental implant immediately after extraction, sometimes requiring bone grafts and subsequent implant placement at a later date.

The rocking procedure briefly described above may be difficult to perform when there is little or no crown for the dental professional to grip. For example, in some patients, the crown may be sufficiently deteriorated, or not sufficiently extended above the alveolar bone to enable a dental professional to grip the crown. In these cases, specialized tools may be used to remove bone to allow gripping of the remaining tooth structure. For example, a drill may be used to drill into the alveolar bone in the space surrounding the tooth being removed to expose more of the tooth. Drilling the bone may result in undesired bone removal. In some cases, the drilled out bone material must then be replaced with graft material and the patient must wait for the damaged alveolar bone to heal. For example, when a patient is to receive a dental implant, the patient may have to return after the tooth socket has healed to receive the implant. The pain and potential complications associated with the bone graft procedure and the delay in installation of the implant may be undesirable for both the patient and the dental professional.

Some dental professionals use manual periotomes during extraction of a tooth. Manual periotomes may be configured with a shaped tip disposed at an end of a shaft. In use, the tip may be placed at the base of the crown adjacent the periodontal ligament space. The dental professional then applies force on the shaft to force the tip into the periodontal space. A great amount of force may be required to use the manual periotome and the dental professional's hand and arm may be fatigued by the process.

As described above, a variety of special tools and techniques have been developed to improve tooth extraction. Such tools may be specialized for single purpose use. For example, in a tooth extraction and implantation procedure, separate instruments may be required to extract the tooth, collect the bone graft material, prepare the implant site and install the implant. The variety of tools may require the dental professional to be familiar with and own multiple different instruments. More than just inconvenient, the use of several different instruments may be expensive for the dental professional.

SUMMARY OF DISCLOSURE

A powered surgical instrument is provided. In some embodiments, the powered surgical instrument may include a housing having a proximal end portion and a distal end portion; a receiver having a proximal end portion and a distal end portion, at least a portion of the receiver is movably received within the housing, the distal end portion of the receiver being configured to receive an expander adapted to expand a tooth socket within a treatment area, wherein the receiver is configured to move between a first receiver position in which the distal end portion of the receiver is adjacent the distal end portion of the housing, and a second receiver position in which the distal end portion of the receiver is spaced from the distal end portion of the housing relative to the first receiver position; a bias assembly operatively connected to the receiver and configured to urge the receiver towards the second receiver position; and an actuator disposed within the housing and configured to move the receiver at least from the first receiver position to the second receiver position, wherein the receiver is configured to be selectively moved between the first and second receiver positions independent of the actuator.

In some embodiments, the powered surgical instrument may include a housing having a proximal end portion and a distal end portion; a receiver having a proximal end portion and a distal end portion, at least a portion of the receiver is movably received within the housing, the distal end portion of the receiver being configured to receive an expander adapted to expand a tooth socket within a treatment area, wherein the receiver is configured to move between a first receiver position in which the distal end portion of the receiver is adjacent the distal end portion of the housing, and a second receiver position in which the distal end portion of the receiver is spaced from the distal end portion of the housing relative to the first receiver position; a bias assembly operatively connected to the receiver and configured to urge the receiver towards the second receiver position, wherein the receiver is configured to be moved from the second receiver position to the first receiver position by pushing the expander against the treatment area against urging from the bias assembly; and an actuator disposed within the housing and configured to move the receiver at least from the first receiver position to the second receiver position, wherein the actuator is configured to allow a user to tactilely discriminate when the receiver moves from the first receiver position to the second receiver position and to tactilely discriminate a rigidity of a portion of the treatment area that the expander has contacted relative to a rigidity of at least another portion of the treatment area that the expander has contacted.

In some embodiments, the powered surgical instrument may include a housing having a proximal end portion and a distal end portion; a receiver having a proximal end portion and a distal end portion, at least a portion of the receiver is slidingly received within the housing, the distal end portion of the receiver being configured to receive an expander adapted to expand a tooth socket within a treatment area, wherein the receiver is configured to slide between a first receiver position in which the distal end portion of the receiver is adjacent the distal end portion of the housing, and a second receiver position in which the distal end portion of the receiver is spaced from the distal end portion of the housing relative to the first receiver position; a bias assembly operatively connected to the receiver and configured to urge the receiver towards the second receiver position, wherein the receiver is configured to be slid from the second receiver position to the first receiver position by pushing the expander against the treatment area against urging from the bias assembly; and an actuator disposed within the housing and configured to slide the receiver at least from the first receiver position to the second receiver position, wherein the actuator includes a plunger configured to slide from a first position in which the plunger is spaced from the proximal end portion of the receiver, to a second position in which the plunger contacts the proximal end portion of the receiver when the receiver is in the first receiver position, and to a third position in which the plunger slides the receiver from the first receiver position to the second receiver position when the plunger contacts the proximal end portion of the receiver in the second position.

BRIEF DESCRIPTION OF THE DRAWINGS

FIG. 5 is a perspective view of another embodiment of a powered surgical instrument of the present disclosure.

FIG. 7 is a cross-sectional view of the expander in FIG. 5.

FIG. 8 is a schematic illustration of a dental implant site preparation device according to an embodiment of the disclosure.

FIG. 14 is a partial cross-sectional view of the embodiment shown in FIG. 13 taken along lines 14-14 on FIG. 13, showing a plunger in a first position and a receiver in a first receiver position.

FIG. 15 is the partial cross-sectional view of FIG. 14, showing the plunger in the first position and the receiver in the second receiver position.

FIG. 16 is the partial cross-sectional view of FIG. 14, showing the plunger in a second position and the receiver in the second receiver position.

FIG. 17 is the partial cross-sectional view of FIG. 14, showing the plunger in a third position and the receiver in the first receiver position.

FIG. 18 is a partial view taken along line 18 in FIG. 14 showing the receiver in the first receiver position.

FIG. 19 is a partial view taken along line 19 in FIG. 15 showing the receiver in the second receiver position.

DETAILED DESCRIPTION OF THE DISCLOSURE

Figure 1:
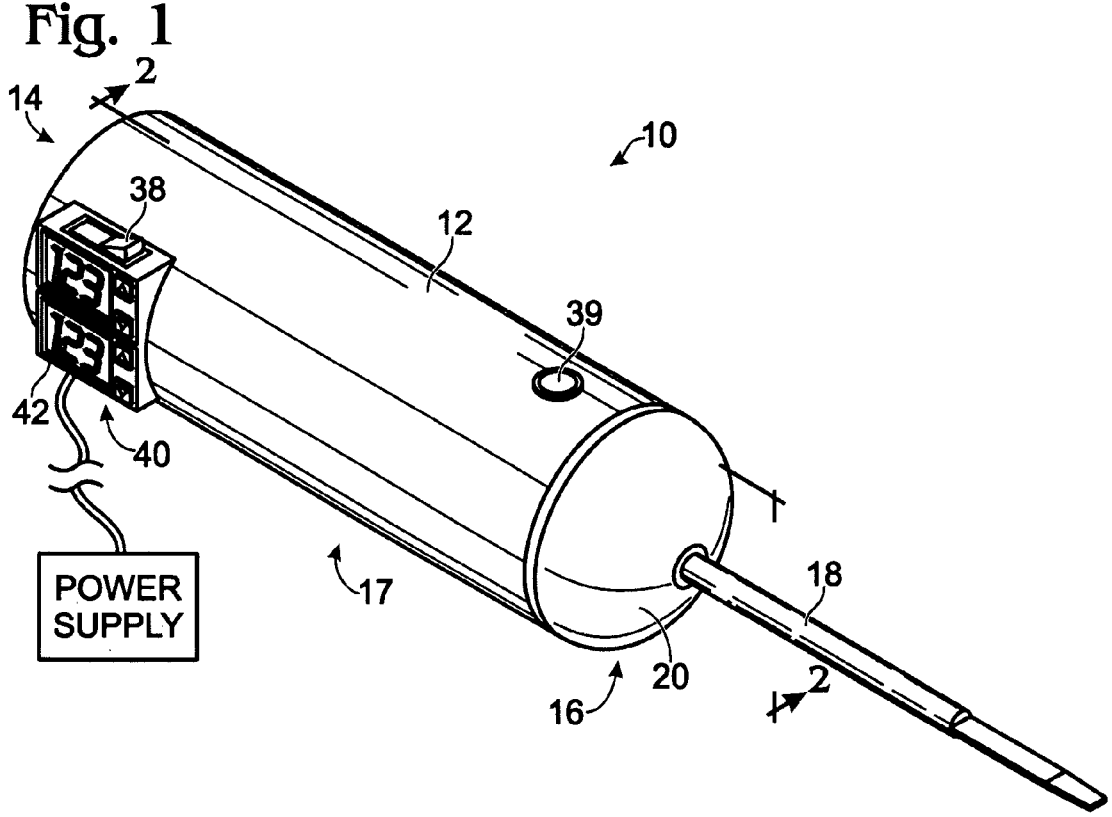
FIG. 1 is a perspective view of an embodiment of a powered surgical instrument of the present disclosure.

FIG. 1 illustrates, somewhat schematically, a perspective view of a powered surgical instrument according to one embodiment of the present disclosure. The powered surgical instrument described below may be used in any suitable dental or medical application, including, for example, extraction of teeth and dental implant procedures. Further, such powered surgical instrument may be used in both human medical and dental applications, as well as veterinary medical and dental applications.

The drawings depict a plurality of embodiments for the powered surgical instrument and reference characters may refer to corresponding elements throughout multiple views. Similarly, the drawings are intended to show illustrative embodiments that depict a variety of elements and subelements. The elements and/or subelements described may be selectively embodied in devices according to the present disclosure alone or in combination with one or more other elements and/or subelements, regardless of whether the particular selected element, subelement, or combination thereof is specifically illustrated in the figures. For example, the powered surgical instrument disclosed herein may include any of the described and/or illustrated actuation controls, actuators, power supplies, tips, etc., regardless of the particular combination shown in a specific figure.

As shown in FIG. 1, powered surgical instrument 10 may include a housing 12. Housing 12 may be configured as a cylindrical body as shown or it may have other suitable configurations. At least a portion of housing 12 may be contoured to be comfortably held in the hand of a dental professional. For example, the housing may be ergonomically designed to substantially correspond to a user's grip. Additionally, housing 12 may be provided with gripping features and/or padding to increase the dental professional's comfort and/or ability to grip the housing. Although not described in detail herein, housing 12 may include additional features to increase its functionality and/or its cooperation with other dental instruments and apparatus, such as holders, chargers, power supplies, etc.

Housing 12 may include a proximal end portion 14 and a distal end portion 16. Distal end portion 16 may be configured to receive an expander 18. In some embodiments, distal end portion 16 may be configured to selectively receive one of a plurality of tools configured to perform one or more surgical functions. Expander 18, as well as the plurality of selectively receivable tools, will be described in more detail below.

Additionally, housing 12 may include an inner portion 15 and an outer portion 17. The inner portion may be adjacent the expander and/or the receiver, while the outer portion may be adapted to be held by a user (as discussed above). Inner portion 15 and/or outer portion 17 may be configured to transmit one or more forces from the expander and/or receiver to the user. For example, the inner and/or outer portions may at least substantially be made of one or more metals, such as stainless steel and/or titanium. Additionally, or alternatively, the inner and/or outer portions may be at least substantially free from one or more dampening members that are adapted to absorb one or more forces transmitted by the expander and/or the receiver, such as rubber guards, etc.

Although inner portion 15 and outer portion 17 are discussed to be at least substantially made of stainless steel and/or titanium, one or both of those portions may alternatively, or additionally, be at least substantially made of any suitable materials configured to transmit one or more forces from the expander and/or the receiver to the user holding the outer portion. Additionally, although inner portion 15 and outer portion 17 are discussed to be at least substantially free from one or more dampening members, one or both portions may include one or more dampening members.

Powered surgical instrument 10 also may include a receiver 20 having a proximal end portion 19 and a distal end portion 21. The distal end portion may be configured to selectively receive an expander in addition to, or as an alternative to, the distal end portion of the housing. In some embodiments, receiver 20 may be adapted to receive one or more of a variety of tools of different dimensions and configurations.

A locking mechanism may be incorporated in distal end portion 16 of housing 12 and/or into distal end portion 21 of receiver 20 to accommodate receipt and securement of the various tools to the instrument. For example, housing 12 and/or receiver 20 may include at least one locking mechanism similar to the adjustable chuck customarily used on power drills in the hardware industry. Additionally, or alternatively, the locking mechanism may include one or more components of the bit holders described in U.S. patent application Ser. No. 11/595,540 entitled "Bit Holders," which was filed on Nov. 9, 2006. The complete disclosure of that application is herein incorporated by reference for all purposes. Alternatively, or additionally, distal end portion 16 and/or receiver 20 may include other clamping mechanisms that will be recognized as suitable for securing differently-sized tools.

Figure 2:
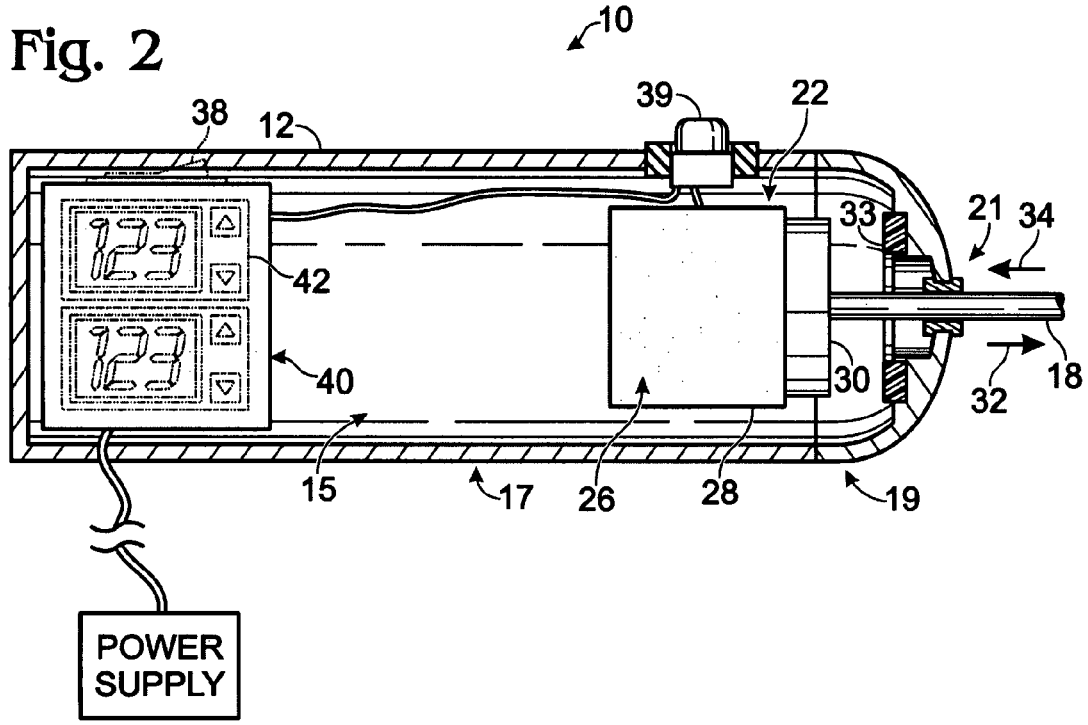
FIG. 2 is a cross-sectional view along line 2-2 schematically illustrating some components of the embodiment shown in FIG. 1.

With reference to FIG. 2, powered surgical instrument 10 may include an actuator 22 disposed within housing 12. As used herein, the term "actuator" includes a device configured to move one or more other components of the surgical instrument, such as expander 18 and/or other tool secured by receiver 20 and/or distal end portion 16. In some embodiments, the actuator may additionally, or alternatively, move at least a portion of the receiver. The movement caused by the actuator may be linear in one direction or it may be linear in a reciprocating, back and forth motion. When actuator 22 causes reciprocating movement, actuator 22 may be referred to as a "reciprocator." Powered surgical instrument 10 may include an actuator 22 configured to move expander 18 in a forward linear motion, such as from a first position to a second position offset from the first position, such as indicated by forward directional arrow 32 in FIG. 2. Alternatively, actuator 22 may be adapted to move expander 18 in a reverse linear motion, such as indicated by reverse directional arrow 34. Thus, the expander may be driven away from the housing 12, toward housing 12 or in both directions. In some embodiments, actuator 22 may be configured to allow a user to select the direction of linear motion, forward 32, reverse 34, or both. In other embodiments, actuator 22 may be configured to alternatingly move expander 22 in both the forward direction and the reverse direction.

Actuator 22 may be any suitable linear driving device. For example, actuator 22 may be a solenoid actuator, a pneumatic actuator, a mechanical actuator, a motor actuator, a sonic actuator (such as an air turbine driven actuator), a magnetorestrictive ultrasonic actuator, a piezoelectric ultrasonic actuator, and/or other suitable actuator(s) capable of causing linear and/or non-linear motion. FIG. 2 illustrates a solenoid actuator 26, which may include a solenoid coil 28 and a plunger 30 configured to slidingly engage the coil. In an illustrative embodiment, solenoid actuator 26 may be configured to move plunger 30 in the forward direction, shown by arrow 32, and allow the force of the dental professional pushing instrument 10 towards one or more portions of the treatment area to move plunger 30 in the reverse direction, shown by arrow 34. Alternatively, solenoid actuator 26 may be adapted to move plunger 30 in the reverse direction or in reciprocating forward and reverse directions. Examples of suitable solenoid actuators include solenoid actuators manufactured by Intersol Industries Incorporated (Bensenville, Ill.), Ledex (Vandalia, Ohio), Magnetic Sensor Systems (Van Nuys, Calif.), and Shih Shin Technology Co., Ltd. (Taiwan).

Solenoid actuator 26 may be configured to reciprocatingly move plunger 30 in the forward direction 32 and the reverse direction 34. Such a configuration may be achieved by using a biasing member to drive the plunger in the reverse direction. Any suitable biasing mechanism may be used, including a spring, a bumper, such as a gasket, a reversal of the polarity of the solenoid coil, and/or by other means. In the embodiment illustrated in FIG. 2, a rubber gasket 33 is illustrated forward of plunger 30. Rubber gasket 33 may be configured to rebound plunger 30 in the reverse direction preparing it for subsequent movement in the forward direction by actuator 22.

In some embodiments, a bi-directional solenoid may be incorporated within the housing. The bi-directional solenoid may decrease the fatigue experienced by a dental professional and may allow for increased functionality of the instrument. In an embodiment of surgical instrument 10 where the solenoid is bi-directional, solenoid actuator 26 may be operatively coupled to expander 18 such that the reverse motion of plunger 30 also pulls expander 18 in the reverse direction 34.

Actuator 22 may be configured to linearly drive expander 18 to enable a dental professional to more easily remove a tooth or perform other surgical functions within a treatment area. For example, expander 18 may be configured to be positioned along the periodontal ligament space. In some embodiments, expander 18 may be sized such that it is slightly larger than the periodontal ligament space.

As the actuator moves expander 18 linearly, the alveolar bone surrounding the tooth socket is compressed or compacted, thus expanding the socket along the periodontal ligament space. Expander 18 is thus adapted to expand the tooth socket. The linear driving motion of the powered surgical instrument operates with sufficient force to compress the bone surrounding the tooth socket. As a byproduct of the compression of the bone surrounding the tooth socket, the periodontal ligaments may be severed or otherwise broken. Once the bone is sufficiently compressed and the socket is sufficiently expanded, the tooth may be gripped and removed. The linear motion of the powered surgical instrument facilitates the expansion of the tooth socket while minimizing the fatigue that would occur if such a procedure was attempted manually.

With reference to FIGS. 1 and 2, surgical instrument 10 also may include a power supply. The power supply may be external to housing 12, such as an electrical connection between surgical instrument 10 and a standard alternating circuit power supply. Alternatively, the power supply may be disposed within housing 12. In such an embodiment, the power supply may include batteries, either rechargeable or non-rechargeable.

Surgical instrument 10 also may include a power control 38. Regardless of how power is supplied to surgical instrument 10, power control 38 may be configured to allow the dental professional to turn the instrument on or off. Surgical instrument 10 may be considered to be "on" when power is flowing from the power supply to another component of powered surgical instrument 10, such as actuator 22. Power control 38 may be disposed on housing 12 as shown in FIGS. 1 and 2. Alternatively, power control 38 may be disposed external to housing 12, such as on an external control box or other component.

Surgical instrument 10 also may include an actuation or reciprocation control 40. Actuation control 40 may be disposed on or within housing 12 or it may be external to housing 12, such as on an external control box, as will be seen in other embodiments described below. Actuation control 40 is in communication with actuator 22. Actuation control 40 may be configured to enable a user, such as the dental professional, to selectively adjust one or more properties of the actuator and/or other component(s) of the surgical instrument 10.

Actuation control 40 may include a variety of user interfaces and controls, including analog systems and/or digital systems. Actuation control 40 may be a mechanical controller and/or an electronic controller. For example, in FIGS. 1 and 2, surgical instrument 10 is shown with an electronic controller 42. Electronic controller 42 may include one or more LED displays (or other type of electronic display), one or more user input devices, such as touch pads, sliders, or dials, and one or more digital processors to convert the user input into electronic signals.

Actuation control 40 may include other control systems, including analog systems incorporating dials and electrical circuitry rather than digital processing, combinations of analog and digital systems, etc. For example, actuation control 40 may include a combination of digital and analog systems working cooperatively to enable a user to selectively control or adjust the linear motion as generated by actuator 22. Examples of these and other alternative embodiments will be better understood with reference to the description below.

Actuation control 40, in whatever embodiment it is implemented, may be configured to adjust the linear motion induced by actuator 22. For example, actuation control 40 may control one or more of the following characteristics or other like characteristics: the frequency of the linear motion, the intensity of the linear motion, the stroke-length of the linear motion, and/or other characteristic(s) of the motion. With continued reference to the embodiment shown in FIG. 1, expander 18 will move at a given speed (frequency), will travel a certain distance in each direction with each motion (stroke-length), and will travel with a certain force conveyed by actuator 22 (intensity). Other characteristics that may be controlled by actuation control 40 may include such things as modifying one or more of these characteristics over time to create actuation and/or reciprocation patterns. As one example of an actuation pattern, a user may prefer a lower frequency, intensity, and/or stroke-length at the beginning of the procedure to ensure proper placement of the instrument and prefer a higher frequency, intensity, and/or stroke-length after the expansion is underway and the expander is at least partially maintained in the proper placement by the surrounding tooth and bone.

As an illustration of the use of actuation control 40 to enable a user to selectively control characteristics of the motion generated by actuator 22, the following examples are provided. In some embodiments, actuation control 40 may allow a user to select the frequency at which actuator 22 drives expander 18. In some embodiments, the range of selectable frequencies may range from about 0 Hz to about 40.0 kHz, or anywhere there between. In some embodiments, the upper frequency limit may be 20 kHz, 10 kHz, or 1.0 kHz. Embodiments with a narrower range of selectable frequencies also may be configured. For example, in some embodiments, the selectable range of frequencies may span from about 0 Hz to about 100 Hz. In still other embodiments, the selectable range may span from about 0 Hz to about 60 Hz. Actuation control 40 may be configured to allow a user to select a desired frequency in the range. Alternatively, actuation control 40 may be indexed so that a user can select from a collection of predetermined frequencies within the range.

In some embodiments, actuation control 40 may allow a user to operate actuator 22 such that the actuator moves the expander and/or the receiver at one or more frequencies adapted to allow a user to tactilely discriminate one or more movements of the expander, the receiver, and/or the plunger, such as when the expander moves from the first position to the second position, when the expander moves from the second position to the first position, when the receiver moves from a first receiver position to a second receiver position, when the receiver moves from a second receiver position to a first receiver position, when the plunger moves in the forward direction, and/or when the plunger moves in the reverse direction. For example, the one or more frequencies may include frequencies at or above approximately 5 Hz and/or frequencies at or below approximately 60 Hz. In some embodiments, those frequencies may allow a user to tactilely discriminate when, for example, the receiver moves from the first receiver position to the second receiver position.

Additionally, or alternatively, the one or more frequencies at which the actuator moves the expander and/or the receiver may be adapted to allow a user to tactilely discriminate a rigidity of a portion of a treatment area that the expander has contacted relative to a rigidity of at least another portion of the treatment area that the expander has contacted. For example, the one or more frequencies may include frequencies at or above approximately 5 Hz and/or frequencies at or below approximately 60 Hz. In some embodiments, those frequencies may allow a user to tactilely discriminate when, for example, the expander has contacted a tooth socket relative to contacting gum tissue, cartilage, and/or bone because a patient's bone may be more rigid than the patient's cartilage, which may be more rigid than the patient's tooth socket, which may be more rigid than the patient's gum tissue.

Although the actuator is discussed to be configured to move the expander and/or the receiver at frequencies between approximately 5 Hz and approximately 60 Hz, the actuator may be configured to move the expander and/or the receiver at frequencies above 60 Hz and/or below 5 Hz. Additionally, although the frequencies of the actuator are discussed to allow a user to tactilely discriminate particular movements of one or more components of the powered surgical instrument, those frequencies may additionally, or alternatively, allow the user to tactilely discriminate other movements of one or more components of the powered surgical instrument. Moreover, although the frequencies of the actuator are discussed to allow a user to tactilely discriminate when the expander has contacted a patient's tooth socket, the patient's gum tissue, the patient's cartilage, or the patient's bone, those frequencies may allow the user to tactilely discriminate a rigidity of other portions of the treatment area relative to at least another portion of the treatment area.

Additionally, or alternatively, actuation control 40 may allow a user to select the intensity at which actuator 22 drives the receiver and/or expander 18. In some embodiments, the actuator may drive the expander with up to about 1.5 pounds of force. A user may be able to select an intensity ranging from 0 pounds-force to about 1.5 pounds-force. Alternatively, actuation control 40 may provide an index of selectable intensities within the range (and/or outside that range). In other embodiments, actuator 22 may drive expander 18 with a lower maximum force, such as 0.75 pounds-force or 1.0 pounds-force. Although the actuator is discussed to drive the receiver and/or the expander with particular force(s), the actuator may be configured to drive the receiver and/or the expander with any suitable force(s), such as one or more forces greater than 1.5 pounds-force.

In some embodiments, actuation control 40 may enable a user to select the stroke-length that actuator 22 provides expander 18. As described above, in the embodiments where a solenoid actuator is used, actuation control 40 may adjust the stroke-length by modifying the extent to which plunger 30 is driven in the forward direction (represented by arrow 32), by modifying the amount of rebound force provided by a biasing force, and/or by adjusting the position of the solenoid actuator 26 within housing 12. In some embodiments, the user may be able to select a stroke-length ranging from about 0.01 mm to about 1.0 mm or anywhere there between. In other embodiments, the stroke-length may be selectable within a range from about 0.01 mm to about 0.5 mm. Although actuation control 40 is discussed to adjust stroke-length between particular ranges, the actuation control may be configured to adjust stroke-length among any suitable ranges, including ranges outside the particular ranges described above.

Referring back to the figures, in some embodiments, housing 12 may be configured with an operational control 39. Operational control 39 may be disposed on housing 12 to provide additional control and convenience to the dental professional performing the surgical procedure. For example, operational control may be configured to temporarily halt the motion of expander 18 without requiring the dental professional to modify other settings or reach for other controls. The operational control may be configured to cooperate with a portion of actuator 22 or with a portion of expander 18 or both. In some embodiments, operational control 39 may cooperate with power control 38 and/or with actuation control 40. Although shown at the distal end portion 16 of housing 12, operational control 39 may be disposed on any suitable location on the housing of the instrument or accessible component of the instrument.

Figure 3:
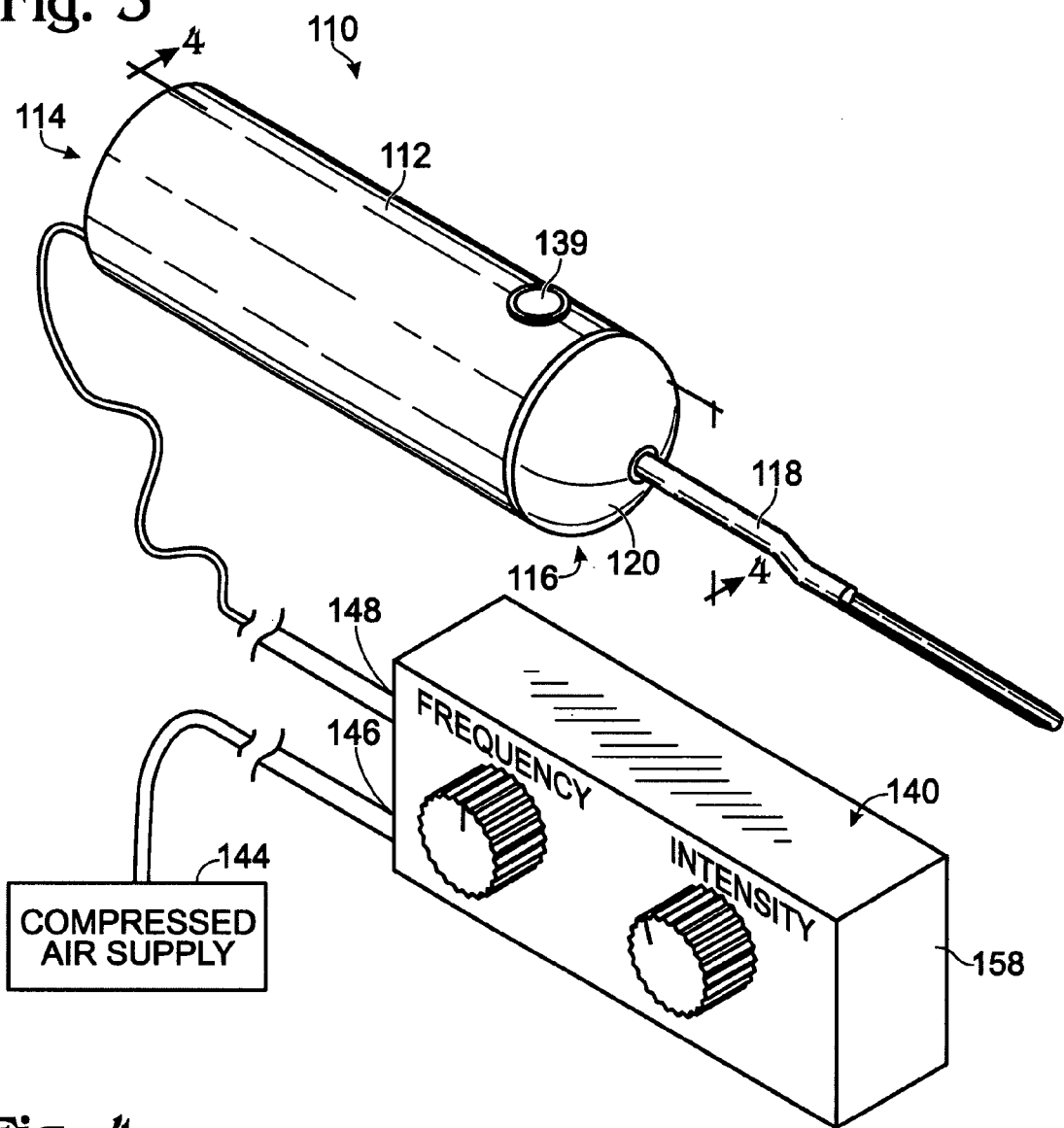
FIG. 3 is a perspective view of another embodiment of a powered surgical instrument of the present disclosure.
Figure 4:
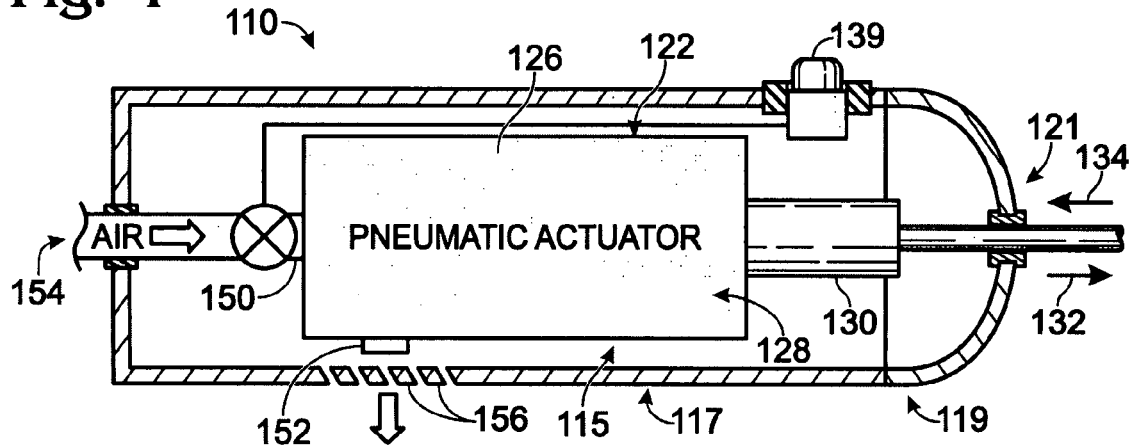
FIG. 4 is a cross-sectional view along line 4-4 schematically illustrating some components of the embodiment shown in FIG. 3.

Referring now to FIGS. 3 and 4, an alternative embodiment of a powered surgical instrument is illustrated in a somewhat schematic perspective view. As described above, components of this embodiment may be interchangeable with the earlier and later described embodiments and are not limited to the combinations as shown in the illustrative figures. As in FIGS. 1 and 2, the powered surgical instrument 110 of FIGS. 3 and 4 includes a housing 112 with a proximal end portion 114, a distal end portion 116, an inner portion 115, and an outer portion 117. Distal end portion 116 may be configured to receive an expander 118. Surgical instrument 110 also may include a receiver 120 having a proximal end portion 119 and a distal end portion 121 as described above. The expander 118 in FIG. 3 has a slightly different configuration than expander 18 of FIG. 1. That difference will be discussed in detail below.

The embodiment shown in FIGS. 3 and 4 also includes an actuator 122 to move expander 118. Like in the embodiment shown in FIGS. 1 and 2, actuator 122 may be configured to move expander 118 in a linear motion. However, actuator 122 of the embodiment illustrated in FIGS. 3 and 4 is a pneumatic actuator 126 as opposed to solenoid actuator 26 of FIGS. 1 and 2. Pneumatic actuator 126 may include one or more pneumatic devices, represented schematically at 128, capable of pneumatically moving plunger 130 to move expander 118 in a linear motion. As with solenoid actuator 26, pneumatic actuator 126 may be configured to drive plunger 130 in the forward direction, shown by arrow 132, in the reverse direction, shown by arrow 134, or in both the forward and the reverse directions, either selectively or alternatingly.

Surgical instrument 110 incorporating pneumatic actuator 126 also may include a compressed air supply 144 in communication with pneumatic actuator 126. Compressed air supply 144 may supply a stream of compressed air to an actuation control 140. For example, as shown in FIG. 3, actuation control 140 may have an air input 146 and an air output 148. Alternatively, compressed air supply 144 may provide compressed air directly to housing 112 and pneumatic actuator 126. In some embodiments, pneumatic actuator 126 or actuation control 140 may be configured with a plurality of valves, channels, and other components adapted to allow a user to selectively control the linear motion provided by the actuator, such as forward only, reverse only, or reciprocating motion.

Air from compressed air supply 144 may be directed into instrument 110. For example, as shown in FIG. 4, pneumatic actuator 126 may include a housing air inlet 154, an air feed 150, and an air vent 152. Housing 112 also may include an air vent 156. In some embodiments, actuation control 140 will control the air supply to pneumatic actuator 126 to cause plunger 130 to drive expander 118 in a linear motion. Alternatively, a steady stream of compressed air may be provided to pneumatic actuator 126 and the pneumatic actuator may control the movement of plunger 130.

As shown in FIG. 3, actuation control 140 may include one or more controls to allow a user to selectively adjust the linear motion as described above. For example, in the illustrated embodiments, actuation control 140 may include user-maneuverable dials that may be selectively adjusted during a procedure. Similar to the embodiments shown in FIGS. 1 and 2, actuation control 140 may be used to selectively control the frequency of actuation, the intensity of actuation, or the stroke-length, as well as other characteristics. Actuation control 140 may be part of a separate control box 158 or, in some embodiments, one or more of the controls may be disposed on housing 112. Additionally, compressed air supply 144 may be a separate component as shown in FIG. 3 or it may be incorporated into control box 158.

When powered surgical instrument 110 is pneumatically driven as in FIGS. 3 and 4, the power supply and power control may be different from the power supply and power control described in connection with the embodiment illustrated in FIGS. 1 and 2. For example, there may be several power controls that cooperate to determine when pneumatic actuator 126 actually moves or drives expander 118. For example, in some embodiments, there may be a power control on compressed air supply 144, a power control on control box 158, a power control associated with actuation control 140, a power control on housing 112, a power control associated with pneumatic actuator 126, a power control associated with more than one of these components, etc. One or more power controls may cooperate to control when actuator 122 moves expander 118 in a linear motion. Additionally, one or more of these power controls may be configured as an operational control 139 (as discussed above in regards to operational control 39) to temporarily secure expander 118 in a fixed location while not interfering with the operation of the remaining components.

FIG. 5 illustrates another embodiment of the powered surgical instrument of the present disclosure. As described above, components of this embodiment may be interchangeable with the earlier and later described embodiments and are not limited to the combinations as shown in the illustrative figures. In FIG. 5, both actuation control 240 and power source 236 are external to housing 210. Further, actuation control 240 is shown as a digital readout, but the dials of FIG. 3 or other like controls may be used without departing from the scope of the disclosure.

FIG. 5 further illustrates an embodiment wherein powered surgical instrument 210 includes a pressure sensitive device, such as foot pedal 260. The pressure sensitive device may be a foot pedal as shown, but also may include other pressure sensitive devices, such as a touch pad disposed on housing 212. In some embodiments, foot pedal 260 may cooperate with actuation control 240 to allow a user additional control over the linear motion during the surgery or procedure. In this way, pressure sensitive device 260 is similar to operational control 39, 139. However, in addition to the start/stop functions of operational control 39, foot pedal 260 may be adapted to allow a user to variably control one or more characteristics, such as frequency, intensity, etc.

For example, foot pedal 260 may be configured to allow a user to adjust the frequency of the motion by applying more or less pressure. In some embodiments, powered surgical instrument may be provided with more than one pressure sensitive device, such as a foot pedal and a touch pad. The pressure sensitive device that may be a component of powered surgical instrument 210 may be adapted to cooperate with actuation control 240 to allow adjustment up to set maximum. For example, when foot pedal 260 is used to adjust the frequency of linear motion, actuation control 240 may be adapted to allow a user to set a maximum frequency and foot pedal 260 may be configured to allow the user to vary the frequency between 0 Hz and the maximum frequency set on actuation control 240.

FIGS. 6-10 illustrate an embodiment of powered surgical instrument adapted to prepare a tooth socket for a dental implant. As described above, components of this embodiment may be interchangeable with the earlier and later described embodiments and are not limited to the combinations as shown in the illustrative figures. As in the embodiments described above, the surgical instrument of FIG. 6 may include a housing 312. Housing 312 may include a receiver (indicated generally at 320) configured to selectively receive a dental implant site preparation device 318. The actuator (as indicated by general arrow 322) may be any suitable actuator configured to drive the dental implant site preparation device 318 linearly.

Figure 6:
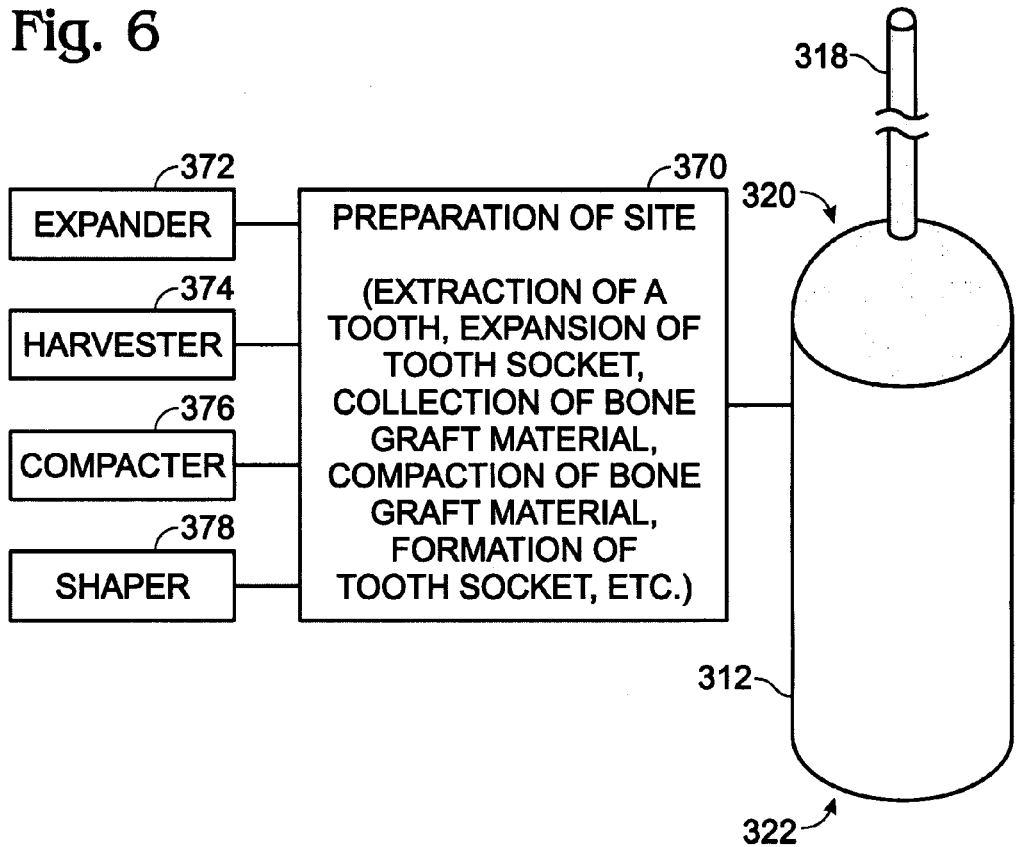
FIG. 6 is a schematic view of a surgical instrument according to another aspect of the present disclosure.
Figure 9:
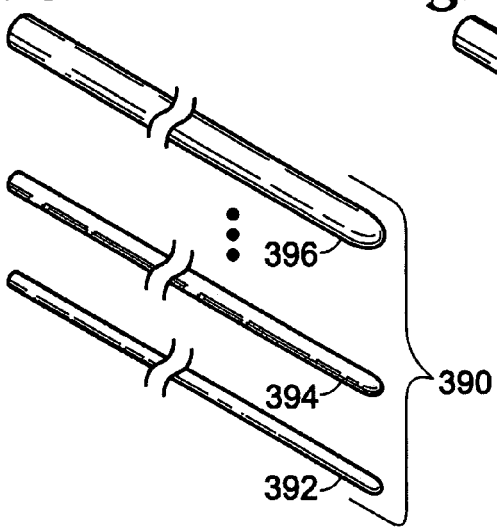
FIG. 9 is a cross-sectional view of an alternative dental implant site preparation device that may be used in cooperation with a powered surgical instrument of the present disclosure.

FIG. 6 illustrates a dental implant site preparation device 318 somewhat schematically. The expander described above is an example of a dental implant site preparation device 318 and that the above description of surgical instruments, actuators, and expander motion also may describe the surgical instrument of FIG. 6 and dental implant site preparation device 318.

The procedure for installing a dental implant often begins with extraction of the natural tooth to make way for the implant. However, the natural tooth socket is generally not naturally prepared to receive a dental implant. For example, the alveolar bone material around the tooth socket may not be able to securely hold the implant or the tooth socket may not be properly shaped to receive the implant.

Illustrative steps for preparing a dental implant site are summarized in box 370 of FIG. 6. For example, such steps may include removing or extracting a resident tooth, expanding the tooth socket, collecting bone graft material, compacting bone graft material into the tooth socket and forming the tooth socket to the proper shape. Additionally, when bone graft material is utilized, the dental professional may treat the placement area to facilitate proper healing. For example, the bone graft placement area may be covered with a protective membrane that is secured to the surrounding bone using bone tacks.

As illustrated in FIG. 6, a powered surgical instrument may be used to prepare a dental implant site by selectively securing a dental implant site preparation device 318 to housing 312. One illustrative dental implant site preparation device may include an osteotome. The osteotome as an implant site preparation device may be used in several applications, such as for soft bone to form the site by compressing the bone lateral, which causes a denser bone to implant interface rather than removing valuable bone from the surgical site, and/or ridge splitting and/or expansion. A variety of additional site preparation devices may be used in cooperation with the disclosed powered surgical instrument, some of which include an expander 372, a harvester 374, a compacter 376, and a shaper 378. A single site preparation device may be configured to perform more than one function, such as compaction of bone material and shaping of the tooth socket.

Expander 372 may be used to extract the tooth from the tooth socket, as discussed above. For example, expander 372 may be configured to have a width slightly larger than the width of the periodontal ligament space. When expander 372 is slightly larger than the periodontal ligament space, the linear motion of the expander compresses or compacts the alveolar bone surrounding the tooth socket expanding the socket. Additionally, as the socket expands and expander 372 is moved further into the periodontal ligament space, expander 372 may be adapted to cut or sever the periodontal ligaments. Embodiments of expander 372 are illustrated in FIGS. 1, 3, and 5 as expander 18, 118, and 218 respectively.

Expander 372 may be adapted to have a relatively flat distal end portion as shown in FIG. 1.

Alternatively, expander 372 may have a contoured distal end portion as shown in FIGS. 3 and 5. A cross-section of the contoured distal end portion is illustrated in FIG. 7, which is a cross-sectional view of expander 218 in FIG. 5. Contoured expander 218 may be adapted to substantially correspond with the contours of an average tooth. Contoured expander 218 may be formed in a u-shaped configuration having a bottom portion 262 and a pair of raised portions 264*a*, 264*b*.

Additionally, expander 372 may be configured with a bayonet tip as shown in FIG. 5. Some embodiments of the implant site preparation device include one or more bends in the shaft. Such bends in the shaft may be similar to those shown in FIG. 5 or may include other bends and configurations of the shaft to enable the dental professional to better access the surgical site.

Expander 372 may include a variety of devices configured to facilitate removal of a tooth and/or preparation of a tooth socket for a dental implant. Expander 372 is adapted to expand the periodontal ligament space and may be configured to have width at the distal end portion greater than the width of the periodontal ligament space. On average, the periodontal ligament space ranges from 0.25 mm to 0.4 mm. Expanders 372 of the present disclosure may have a width at the distal end portion ranging from about 0.25 mm to about 0.75 mm.

With continued reference to FIG. 6, the powered surgical tool disclosed herein also may be used with a harvester. Harvester 374 may be used to collect bone fragment material. An illustrative harvester is illustrated in FIG. 8 and includes a shaft 382 having a distal end portion 384 and a proximal end portion 386. Harvester 374 also may include one or more scrapers 388 disposed adjacent to distal end portion 384. In use, harvester 374 may be used to collect bone fragment material by placing scrapers 388 in contact with a surface of a bone Harvester 374 may be received within the powered surgical instrument described herein such that the harvester is driven in a collection direction (e.g. toward the housing) to coincide with the configuration of scrapers 388. However, harvester 374 also may be used in cooperation with a surgical instrument configured to drive in a forward direction if scrapers 388 were configured accordingly. The driven motion of harvester 374 coinciding with the configuration of scrapers 388 allows the harvester to collect bone graft material with less effort and fatigue for the dental professional.

A compacter 376 also may be received within the disclosed powered surgical instrument. Compacter 376 may be configured to perform one or more functions. For example, compacter 376 may be configured to pack bone graft material into a tooth socket. Additionally, compacter 376 may be configured to compress bone material surrounding the tooth socket to increase the density of the bone to implant interface to better receive an implant. As mentioned above, an empty tooth socket is not generally naturally prepared for receipt of an implant. Bone graft material is often used to provide the dental professional with material to form a more preferred implant site. The graft material may be compacted into place, such as by repeated impacts from compacter 376.

A shaper 378 also may be received within powered surgical tool 318. Shaper 378 of FIG. 6 may include a set of site shaping devices 390 illustrated in FIG. 9. A set of site shaping devices 390 may include one or more shapers 392, 394, 396. Each shaper 392, 394, 396 may be configured to perform one or more functions similar to those of compacter 376. For example, site-shaping devices 390 may be configured to pack bone graft material into a tooth socket. Additionally, site-shaping devices may be configured to compress bone material surrounding the tooth socket to densify the bone to implant interface. As shown, the shapers have a rounded distal end portion but the distal end portion may be configured to meet particular needs or desires of patients or dental professionals. For example, the shapers may be tapered to form the site into the proper shape for receiving the dental implant. The difference between shaper 378 and compacter 376 will be better understood with reference to the following discussion.

Once the graft material is compacted into the socket or when graft material is not used, it may still be desirable to shape the tooth socket. A natural tooth socket may be oblong or elliptical and many dental implants are circular. Accordingly, dental implant site preparation may include forming the tooth socket to correspond with the dental implant. For example, bone graft material may be compacted into a socket leaving a socket opening that may be smaller than required to receive the implant. A hole the size of the implant may be drilled into the graft material but the edges of the hole may not be dense enough or stable enough to secure an implant.

A compression and expansion process may be used to form the tooth socket for receiving an implant and to increase the density of socket. In such a process, a hole smaller than the diameter of the implant may be drilled to start the forming process. For example, the dental implant may have a diameter of 5.0 millimeters and a 2.0 millimeter hole may be drilled in the filled-in tooth socket. Subsequently, a 3.5 mm diameter shaper 392 may be driven into the 2 mm hole. Each of the shapers 392, 394, 396 may have a tapered distal end portion to allow the larger compactor to start into the hole prepared by the smaller compacter. The impact of the larger diameter shaper into the hole compresses the bone graft material outwardly, densifying the bone and forming the implant site. Shaper 392 may be driven by powered surgical instrument in a forward direction or in reciprocating motion to reduce the fatigue on the dental professional. Shaper 392 will form a 3.5 mm hole in the filled-in tooth socket. Shaper 394 may then be driven into the filled-in tooth socket by the surgical instrument. Shaper 394 may have a 4.3 mm diameter and may compress the bone enlarging the tooth socket to 4.3 mm in diameter. The process of expanding a hole in the filled-in tooth socket may continue until the hole reaches the desired diameter. For example, shaper 396 may have a diameter of 5.0 mm to prepare a dental implant site for a 5.0 mm diameter implant.

Figure 10:
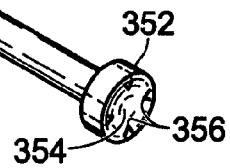
FIG. 10 is a perspective view of another dental implant site preparation device that may be used in cooperation with a powered surgical instrument of the present disclosure.

Another dental implant site preparation device 318 is illustrated in FIG. 10. Tack driver 350 may be adapted to drive tacks into bone surrounding a bone-graft placement area. For example, typically, once bone graft material is placed in the implant site from a collection area, the placement area needs to heal. As discussed above, a dental professional may place a protective membrane over the placement area to allow the bone to grow back (rather than being displaced by faster growing soft tissue). The protective membrane may be secured to the bone with bone tacks.

Tack driver 350 may facilitate the securement of the protective material through the repetitive linear motion of the powered surgical instrument disclosed herein. Tack driver 350 may be configured to have a blunt head 352 as shown in FIG. 10. Blunt head 352 may have a flat surface or it may be configured with a slight concavity 354 as illustrated. Blunt head 352 also may be configured with a plurality of flanges 356 within concavity 354. A tack may be positioned within concavity 354 on blunt head 352. Flanges 356 may secure the tack. The powered surgical instrument may then be positioned to drive the tack into place. Once the bone tack is started into the bone, the flanges will release the tack and the actuator will continue to smoothly drive the tack into the bone.

Figures 11, 12:
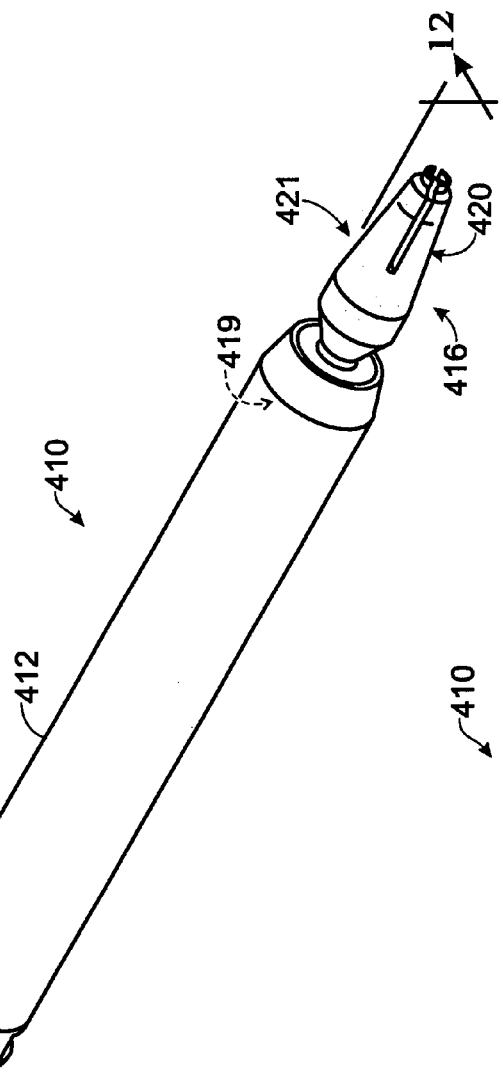
FIG. 11 is a perspective view of one embodiment of a powered surgical instrument of the present disclosure.
FIG. 12 is a cross-sectional view of the embodiment shown in FIG. 11.

FIGS. 11 and 12 illustrate an alternative embodiment of a powered surgical instrument. The instrument shown in FIGS. 11 and 12 are illustrative only and may be combined with one or more of the features and aspects described above and below. FIG. 11 illustrates a perspective view of powered surgical instrument 410 according to the present disclosure. As shown in FIG. 11, powered surgical instrument 410 includes a housing 412 having a proximal end portion 414, a distal end portion 416, an inner portion 415, and an outer portion 417. The powered surgical instrument also may include a receiver 420 having a proximal end portion 419 and a distal end portion 421.

FIG. 12 illustrates a cross-sectional view of the embodiment illustrated in FIG. 11. Receiver 420 may include a tool holder portion 441 and a shaft portion 443. The tool holder portion may include any suitable structure configured to removably hold and/or secure an expander and/or other tool (s). For example, tool holder portion 441 may include one or more components of the tool holders described in U.S. patent application Ser. No. 11/595,540 entitled "Bit Holders," which was filed on Nov. 9, 2006. The complete disclosure of that application has been incorporated by reference for all purposes.

Shaft portion 443 may include any suitable structure operatively connected to the housing. For example, the shaft portion may be movably received within the housing, such as slidingly, pivotally, and/or rotatably received. Additionally, or alternatively, shaft portion 443 may be configured to move (such as slide) among a plurality of positions. For example, shaft portion 443 may be configured to move between a first receiver position in which distal end portion 421 of receiver 420 may be adjacent distal end portion 416 of housing 412, and a second receiver position in which the distal end portion of the receiver may be spaced from the distal end portion of the housing relative to the first receiver position, as shown in FIG. 12.

In some embodiments, the receiver may be configured to be selectively moved between the first and second receiver positions, which may be independent of an actuator. For example, surgical instrument 410 may include at least one bias assembly 445, which may be operatively connected to the receiver and may be configured to urge the receiver towards the first receiver position and/or the second receiver position.

In some embodiments, the bias assembly may allow a user to selectively move the receiver between the first and second receiver positions, which may be independent of an actuator moving the expander and/or receiver. Additionally, or alternatively, the bias assembly may allow a user to selectively move the receiver between the first and second receiver positions, which may be independent of a user holding the expander and/or the receiver to move the expander and/or the receiver. For example, a user may move the receiver from the second receiver position to the first receiver position by pushing the instrument and/or expander against the treatment area against urging from the bias assembly, and/or may move the receiver from the first receiver position to the second receiver position by releasing the instrument and/or expander from the treatment area and allowing the bias assembly to urge the receiver from the first receiver position to the second receiver position.

Although the receiver is discussed to move between first and second receiver positions, the receiver may be configured to move among any suitable positions. Additionally, although the receiver is shown to include tool holder portion 441 and shaft portion 443, the receiver may include any suitable structure configured to removably hold or secure a tool.

Within the housing 412, powered surgical instrument 410 is illustrated as including an actuator 422 operatively associated with receiver 420 to move dental implant site preparation devices that may be received therein. Actuator 422 is illustrated as a solenoid actuator 426, including a solenoid coil 428 and a plunger 430. Additionally, actuator 422 is shown including biasing member 433 to drive the reverse linear motion of plunger 430. In the embodiment of FIG. 12, biasing member 433 includes one or more springs. The actuator may be configured to move the receiver between the first receiver position to the second receiver position.

Additionally, or alternatively, the actuator may be configured to allow a user to tactilely discriminate particular operation(s), movement(s), force(s), and/or other operating parameter(s), such as when the receiver moves from the first receiver position to the second receiver position, and/or a rigidity of a portion of the treatment area that a expander has contacted relative to a rigidity of at least another portion of the treatment area that the expander has contacted. For example, the plunger may be configured to move from a first position in which the plunger may be spaced from the proximal end portion of the receiver, to a second position in which the plunger may contact the proximal end portion of the receiver when the receiver is in the first receiver position, and to a third position (shown in FIG. 12) in which the plunger may move the receiver from the first receiver position to the second receiver position when the plunger contacts the proximal end portion of the receiver in the second position. In some embodiments where the plunger includes one or more positions in which it does not contact the receiver, the actuator may be referred to as being "decoupled" from the receiver and/or having a "decoupled structure." In some embodiments, the decoupled structure may allow a user to tactilely discriminate particular operation(s), movement(s), force(s), and/or other operating parameter(s), such as those discussed above.

Figure 13:
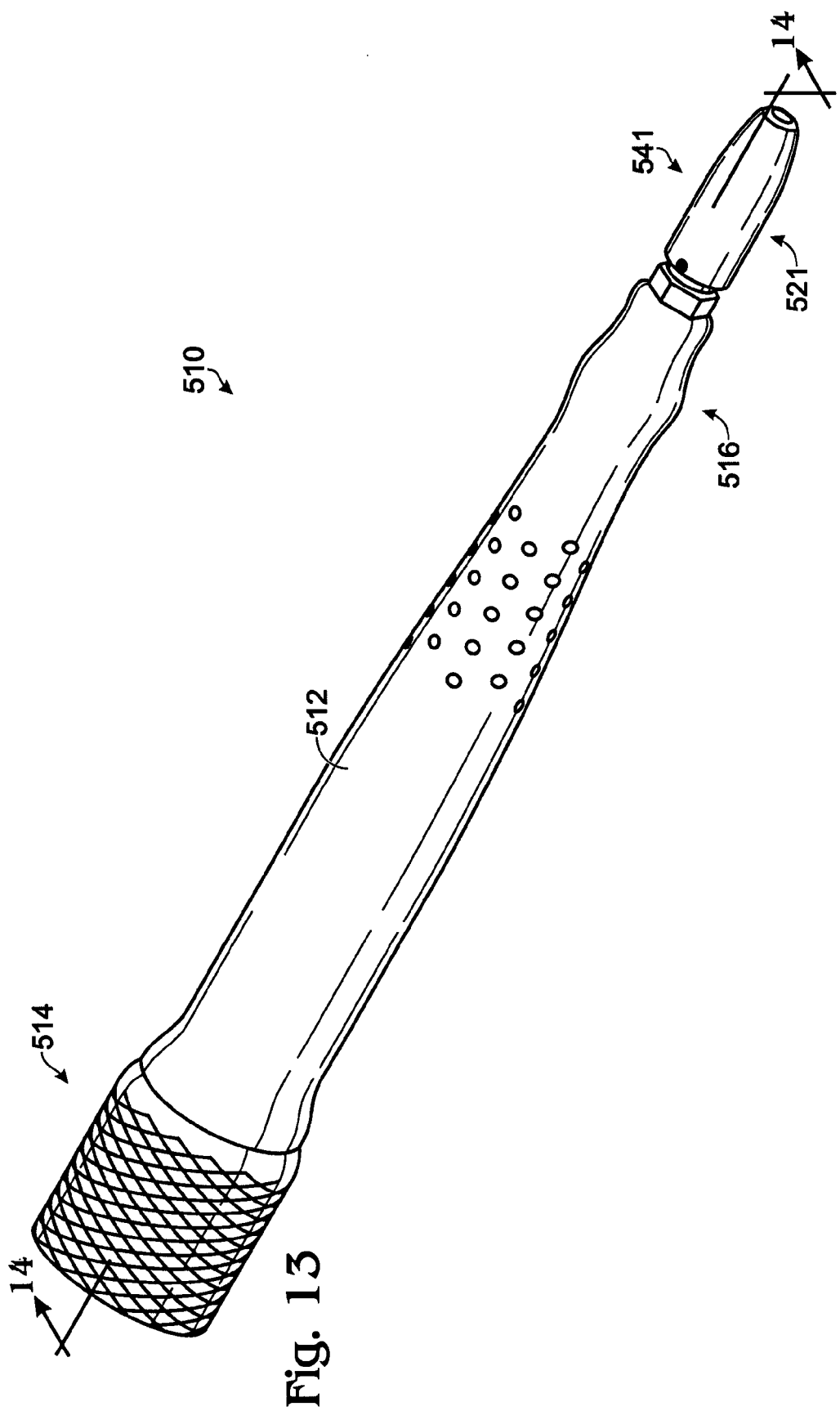
FIG. 13 is a perspective view of one embodiment of a powered surgical instrument of the present disclosure.

FIGS. 13-19 illustrate an alternative embodiment of a powered surgical instrument. The instrument shown in FIGS. 13-19 is only an illustrative example and may be combined with one or more of the features and aspects described above. FIG. 13 illustrates a perspective view of powered surgical instrument 510 according to the present disclosure. As shown in FIG. 13, powered surgical instrument 510 may include a housing 512 having a proximal end portion 514 and a distal end portion 516. Additionally, the powered surgical instrument may include a receiver 520 having a proximal end portion 519 and a distal end portion 521.

FIGS. 14-19 illustrate a cross-sectional view of the embodiment illustrated in FIG. 13. Housing 512 may include any suitable structure configured to contain one or more other components of the surgical instrument and/or to provide tactile feedback to a user holding the housing. For example, housing 512 may include an inner portion 515 and an outer portion 517. The inner portion may be adjacent at least a shaft portion of the receiver and/or may be configured to transmit one or more forces from the receiver to outer portion 517. For example, the inner portion may be at least substantially made of one or more metals, such as stainless steel and/or titanium. Additionally, or alternatively, the inner portion may be at least substantially free from one or more dampening members.

Additionally, or alternatively, the inner portion of the housing may include one or more support members 524, which may include any suitable structure configured to support at least a shaft portion of the receiver and/or to transmit one or more forces from the receiver to the outer portion of the housing. For example, the support members may include one or more flange bushings 525. The flange bushings may at least substantially include any suitable materials, such as polyetheretherketone.

Although flange bushings 525, are discussed to at least substantially include polyetheretherketone, the flange bushings may alternatively, or additionally, include any suitable materials. Additionally, although support members 524 is shown to include flange bushings 525, the support members may alternatively, or additionally, include any suitable structure configured to support at least a shaft portion of the receiver and/or to transmit one or more forces from the receiver to the outer portion of the housing.

Moreover, although inner portion 515 is discussed to be at least substantially free from one or more dampening members, the inner portion may include one or more dampening members. Furthermore, although inner portion 515 is discussed to include one or more metals, such as stainless and/or titanium, the inner portion may additionally, or alternatively, include any suitable material(s).

Outer portion 517 may be configured to be held by a user and/or may be configured to transmit one or more forces from inner portion 515 to the user. For example, the outer portion may be at least substantially made of one or more metals, such as stainless steel and/or titanium. Additionally, or alternatively, the outer portion may be at least substantially free from one or more dampening members.

Although outer portion 517 is discussed to be at least substantially free from one or more dampening members, the outer portion may include one or more dampening members. Additionally, although outer portion 517 is discussed to include one or more metals, such as stainless and/or titanium, the outer portion may additionally, or alternatively, include any suitable material(s). Moreover, although housing 512 is discussed to include particular structures configured to provide tactile feedback, the housing may additionally, or alternatively, include any suitable structure(s) configured to provide tactile feedback.

Within housing 512, powered surgical instrument 510 may include at least one actuator 522, which may include any suitable structure operatively associated with receiver 520 and configured to move one or more bits or dental devices (such as an expander 518) that may be received by the receiver. Additionally, or alternatively, the actuator may include any suitable structure configured to allow a user to tactilely discriminate one or more movements of the expander and/or the receiver, such as when the receiver moves from the first receiver position to the second receiver position, and/or a rigidity of a portion of a treatment area that the expander contacted relative to a rigidity of at least another portion of the treatment area that the expander has contacted. For example, actuator 522 may include a solenoid actuator 526, including at least one solenoid coil 528, at least one plunger 530, and at least one biasing member 537, as shown in FIGS. 14-17.

Plunger 530 may move among a plurality of positions. The plunger may be decoupled and/or spaced from the receiver in one or more of those positions. For example, the plunger may move among a first position F, a second position S, and a third position T. In the first position, the plunger may be spaced from proximal end portion 519 of receiver 520. The plunger may be spaced in that position regardless on whether the receiver is in a first receiver position or a second receiver position (further discussed below). In the second position, plunger 530 may contact proximal end portion 519 of receiver 520 when the receiver is in a first receiver position. In the third position, plunger 530 may move receiver 520 from a first position to a second receiver position. Although plunger 530 is shown to move among first position F, second position S, and third position T, the plunger may alternatively, or additionally, be configured to move among any suitable position(s).

The actuator may move the receiver at one or more frequencies adapted to allow a user (such as a user holding the housing) to tactilely discriminate one or more movements of the expander and/or the receiver, such as when the receiver moves from the first receiver position to the second receiver position. Additionally, or alternatively, the actuator may move the receiver at one or more frequencies adapted to allow a user to tactilely discriminate a rigidity of a portion of the treatment area that the expander has contacted relative to a rigidity of at least another portion of the treatment area that the expander has contacted. For example, the actuator may move the receiver at frequencies between approximately 5 Hz to approximately 60 Hz. Although particular frequencies are discussed, the actuator may move the receiver at frequencies below approximately 5 Hz and/or above approximately 60 Hz.

Biasing member 537 may include any suitable structure configured to drive motion of plunger 530. For example, solenoid coil 528 may drive plunger 530 from the first position to the second position and/or to the third position, while biasing member 537 may drive the plunger from the third position to the second position and/or to the first position. Biasing member 537 may include one or more springs, and/or other biasing structures.

Although solenoid actuator 526 is shown to include coil 528, plunger 530, and biasing member 537, the solenoid actuator may include any suitable structure configured to move one or more bits that are secured by receiver 520. Additionally, although actuator 522 is shown to include a solenoid actuator, the actuator may alternatively, or additionally, include any suitable actuator, such as one or more of the other actuators described above.

Receiver 520 may include any suitable structure configured to removably hold and/or secure a tool (such as expander 518) and/or to be moved by actuator 522. For example, receiver 520 may include a tool holder portion 541 and a shaft portion 543. The tool holder portion may include any suitable structure configured to removably hold and/or secure expander 518. For example, tool holder portion 541 may include one or more components of the tool holders described in U.S. patent application Ser. No. 11/595,540 entitled "Bit Holders," which was filed on Nov. 9, 2006. The complete disclosure of that application has been incorporated by reference for all purposes.

Shaft portion 543 may include any suitable structure operatively connected to the housing. For example, the shaft portion may be movably received within the housing. Additionally, or alternatively, shaft portion 543 may be configured to move (such as slide) among a plurality of positions. For example, shaft portion 543 may be configured to move between a first receiver position R in which distal end portion 521 of receiver 520 is adjacent distal end portion 516 of housing 512 (as shown in FIGS. 15-16 and 19), and a second receiver position C in which the distal end portion of the receiver is spaced from the distal end portion of the housing relative to the first receiver position (as shown in FIGS. 14 and 17-18).

Additionally, or alternatively, in the first receiver position, proximal end portion 519 of receiver 520 may be adjacent plunger 530 of solenoid actuator 526. In some embodiments, the plunger may be able to contact the proximal end portion of the receiver and/or move the receiver from the first receiver position to the second receiver position. Additionally, or alternatively, proximal end portion 519 of receiver 520 may be spaced from plunger 530 of solenoid actuator 526 in the second receiver position. In some embodiments, the plunger may not contact and/or move the receiver when the receiver is in the first receiver position regardless of the position of the plunger. In some embodiments, the plunger and the receiver may be referred to as being "decoupled" when the receiver is spaced from the plunger, and "coupled" when the plunger contacts and/or moves the receiver.

Although a substantial portion of the receiver is shown to be slidingly received within housing 512, one or more portions of the receiver may alternatively, or additionally, be pivotally, rotatably, and/or received by the housing in any suitable way. Additionally, although receiver 520 is configured not to be moved by plunger 530 in the second receiver position, the receiver may be configured to be moved by the plunger in the second receiver position. Moreover, although shaft portion 543 and/or receiver 520 is shown to move between the first and second receiver positions, the shaft portion and/or the receiver may alternatively, or additionally, move among any suitable positions. Furthermore, although the plunger and the receiver is discussed to be decoupled in at least one of the plurality of positions, the plunger and the receiver may be coupled in all of the plurality of positions.

Powered surgical instrument 510 also may include a bias assembly 545, as shown in FIGS. 18-19, which may include any suitable structure operatively connected to the receiver and/or configured to urge the receiver towards the second receiver position. For example, the bias assembly may include at least one wave spring 547 that may be configured to urge the receiver towards the second receiver position. The wave spring may be positioned in any suitable location, such as between tool holder portion 541 and housing 512. In some embodiments, the bias assembly may allow a user to maintain the expander at a selected portion of the treatment area while the receiver is moving between the first and second receiver positions.

In some embodiments, the bias assembly may allow a user to selectively move the receiver between the first and second receiver positions, which may be independent of an actuator moving the expander and/or receiver. Additionally, or alternatively, the bias assembly may allow a user to selectively move the receiver between the first and second receiver positions, which may be independent of a user holding the expander and/or the receiver to move the expander and/or the receiver. For example, a user may move the receiver from the second receiver position to the first receiver position by pushing the instrument and/or expander against the treatment area against urging from the bias assembly, and/or may move the receiver from the first receiver position to the second receiver position by releasing the instrument and/or expander from the treatment area and allowing the bias assembly to urge the receiver from the first receiver position to the second receiver position. In some embodiments, the ability to selectively move the receiver between the first and second receiver positions may allow a user to ensure hold the instrument in position while the receiver and/or expander moves among the plurality of positions.

Although bias assembly 545 is shown to include wave spring 547, the bias assembly may include any suitable structure configured to urge the receiver towards the second receiver position. For example, the bias assembly may alternatively, or additionally, include leaf spring(s), spiral spring(s), cantilever spring(s), Belleville spring(s), torsion spring(s), gas spring(s), rubber band(s), etc. Additionally, although bias assembly 545 is shown to be configured to urge the receiver towards the second receiver position, the bias assembly may alternatively, or additionally, be configured to urge the receiver towards the first receiver position and/or other suitable position(s). Moreover, although powered surgical instrument 510 is shown to include housing 512, receiver 520, actuator 522, and bias assembly 545, the powered surgical instrument may include alternatively, or additionally, include any suitable structure configured to removably receive one or more bits and/or move those bits in suitable direction(s).

In operation, the receiver of powered surgical instrument 510 may initially be in the second receiver position and the plunger of the solenoid actuator may initially be in the first position (such as when the solenoid actuator is in a de-energized state), as shown in FIGS. 14 and 18. A user may grasp the outer portion of the housing and may move the instrument in position in the treatment area, such as positioning the expander in the tooth socket. Positioning the instrument and/or resistance from one or more portions of the treatment area may move the receiver from the second receiver position to the first receiver position against the urging of the bias assembly, as shown in FIGS. 15 and 19.

The user may activate the solenoid actuator, which may move the plunger from the first position to the second position in which the plunger may contact the proximal end portion of the receiver, as shown in FIG. 16. The plunger may continue to move from the second position to the third position in which the plunger may move the receiver from the first receiver position to the second receiver position, as shown in FIG. 17. The plunger may return to the first position responsive, at least in part, to de-energizing the solenoid actuator and/or urging from the biasing member, as shown in FIG. 15. Additionally, or alternatively, the receiver may move from the second receiver position to the first receiver position responsive, at least in part, to urging from one or more portions of the treatment area, as shown in FIG. 15. The plunger may again move towards the receiver to move the receiver.

One or more components of the instrument, as discussed above, may allow the user to tactilely discriminate when the receiver moves from the first receiver position to the second receiver position, from the second receiver position to the first receiver position, from the second receiver position to the third receiver position, and/or from the third receiver position to the second receiver position. In some embodiments, that ability to tactilely discriminate movements of the receiver may allow the user to estimate how many times the expander has contacted the treatment area.

Additionally, or alternatively, one or more components of the instrument, as discussed above, may allow a user to tactilely discriminate a rigidity of a portion of a treatment area (and/or other portions of the treatment area) that the expander has contacted relative to a rigidity of at least another portion of the treatment area (and/or other portions of the treatment area) that the expander has contacted. In some embodiments, that ability to tactilely discriminate rigidities of different portions of the tooth socket and/or treatment area may allow the user to properly position the expander in desired portion(s) of the treatment area (such as the tooth socket) without the need to visually verify the proper placement of the expander.

Although the present disclosure includes specific embodiments, specific embodiments are not to be considered in a limiting sense, because numerous variations are possible. The subject matter of the present disclosure includes all novel and nonobvious combinations and subcombinations of the various elements, features, functions, and/or properties disclosed herein. The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment and such features, structures and/or characteristics may be included in various combinations with features, structures and/or characteristics of other embodiments.

In the foregoing specification, the invention has been described with reference to specific embodiments thereof. It will, however, be evident that various modifications and changes can be made thereto without departing from the broader spirit and scope of the invention. The specification and drawings are, accordingly, to be regarded in an illustrative rather than a restrictive sense.

What is claimed is:

1. A powered surgical instrument, comprising:
   a housing having a proximal end portion and a distal end portion;
   a receiver having a proximal end portion and a distal end portion, at least a portion of the receiver is movably received within the housing, the distal end portion of the receiver being configured to receive an expander adapted to expand a tooth socket within a treatment area, wherein the receiver is configured to move between a first receiver position in which the distal end portion of the receiver is adjacent the distal end portion of the housing, and a second receiver position in which the distal end portion of the receiver is spaced from the distal end portion of the housing relative to the first receiver position, wherein a larger part of at least one of the expander and the receiver extends external the housing in the second receiver position relative to the first receiver position;
   an actuator disposed within the housing and configured to move the receiver from the first receiver position toward the second receiver position, the actuator including a biasing member and a plunger configured to move from a first position in which the plunger is retracted and spaced from the proximal end portion of the receiver, to a second position in which the plunger contacts the proximal end portion of the receiver when the receiver is in the first receiver position, and to a third position in which the plunger is fully extended and moves the receiver from the first receiver position toward the second receiver position when the plunger contacts the proximal end portion of the receiver in the second position, the biasing member configured to return the plunger from the third position toward the first position; and
   a bias assembly operatively connected to the receiver and configured to urge the receiver toward the second receiver position when the actuator is configured to move the receiver from the first receiver position toward the second receiver position, wherein the actuator is configured to move the receiver from the first receiver position toward the second receiver position independent of the bias assembly, and the bias assembly is configured to urge the receiver toward the second receiver position independent of the actuator.

2. The device of claim 1, wherein the receiver is configured to be moved from the second receiver position toward the first receiver position by pushing the expander against the treatment area against urging from the bias assembly.

3. The device of claim 1, wherein the actuator is configured to allow the user to tactilely discriminate at least one of (i) when the actuator moves the receiver at least from the first receiver position toward the second receiver position, and (ii) a rigidity of a portion of the treatment area that the expander has contacted relative to a rigidity of at least another portion of the treatment area that the expander has contacted.

4. The device of claim 1, wherein the actuator is configured to move the receiver at one or more frequencies adapted to allow a user to tactilely discriminate at least one of when the receiver moves at least from the first receiver position toward the second receiver position and a rigidity of a portion of the treatment area that the expander has contacted relative to a rigidity of at least another portion of the treatment area that the expander has contacted.

5. The device of claim 4, wherein the one or more frequencies include a frequency of at most approximately 60 Hz.

6. The device of claim 1, wherein the housing includes an inner portion adjacent the receiver and an outer portion adapted to be held by a user, and wherein the inner portion is configured to transmit one or more forces from the receiver to the outer portion, and the outer portion is configured to transmit the one or more forces from the inner portion to a user holding the outer portion.

7. The device of claim 6, wherein at least one of the inner portion and the outer portion is at least substantially made of one or more metals.

8. The device of claim 7, wherein the one or more metals include stainless steel.

9. The device of claim 6, wherein the inner portion of the housing includes one or more support members configured to support the receiver and to transmit one or more forces from the receiver to the outer portion of the housing.

10. The device of claim 9, wherein the one or more support members includes one or more flange bushings.

11. The device of claim 10, wherein the flange bushings include polyetheretherketone.

12. The device of claim 6, wherein the housing is at least substantially free from dampening members adapted to absorb one or more forces transmitted by the receiver.

13. The instrument of claim 1, wherein the bias assembly is spaced from the biasing member.

14. The instrument of claim 13, wherein the bias assembly is positioned external the receiver and the housing.

15. The instrument of claim 14, wherein the bias assembly includes a wave spring.

16. A powered surgical instrument, comprising:
   a housing having a proximal end portion and a distal end portion;
   a receiver having a proximal end portion and a distal end portion, at least the proximal end portion of the receiver is movably received within the housing, the distal end portion of the receiver being configured to receive an expander adapted to expand a tooth socket within a treatment area, wherein the receiver is configured to move between a first receiver position in which the distal end portion of the receiver is adjacent the distal end portion of the housing, and a second receiver position in which the distal end portion of the receiver is spaced from the distal end portion of the housing relative to the first receiver position, wherein a larger part of at least one of the expander and the receiver extends external the housing in the second receiver position relative to the first receiver position;

an actuator disposed within the housing and configured to move the receiver from the first receiver position toward the second receiver position, the actuator including a biasing member and a plunger configured to move from a first position in which the plunger is retracted and spaced from the proximal end portion of the receiver, to a second position in which the plunger contacts the proximal end portion of the receiver when the receiver is in the first receiver position, and to a third position in which the plunger is extended and moves the receiver from the first receiver position toward the second receiver position when the plunger contacts the proximal end portion of the receiver in the second position, the biasing member configured to return the plunger from the third position toward the first position wherein the actuator is configured to allow a user to tactilely discriminate when the receiver moves from the first receiver position toward the second receiver position and to tactilely discriminate a rigidity of a portion of the treatment area that the expander has contacted relative to a rigidity of at least another portion of the treatment area that the expander has contacted; and a bias assembly operatively connected to the receiver and configured to urge the receiver towards the second receiver position when the actuator is configured to move the receiver from the first receiver position toward the second receiver position, wherein the receiver is configured to be moved from the second receiver position toward the first receiver position by pushing the expander against the treatment area against urging from the bias assembly, and wherein the actuator is configured to move the receiver from the first receiver position toward the second receiver position independent of the bias assembly, and the bias assembly is configured to urge the receiver toward the second position independent of the actuator, wherein the bias assembly is spaced from the biasing member.

17. The device of claim 16, wherein the housing includes an inner portion adjacent the receiver and an outer portion adapted to be held by the user, and wherein the inner portion is configured to transmit one or more forces from the receiver to the outer portion, and the outer portion is configured to transmit one or more forces from the inner portion to the user holding the outer portion.

18. The device of claim 17, wherein at least one of the inner portion and the outer portion is at least substantially made of stainless steel.

19. The device of claim 17, wherein the inner portion of the housing includes one or more support members configured to support the receiver and to transmit one or more forces from the receiver to the outer portion of the housing.

20. A powered surgical instrument, comprising:

a housing having a proximal end portion and a distal end portion;

a receiver having a proximal end portion and a distal end portion, at least the proximal end portion of the receiver is slidingly received within the housing, the distal end portion of the receiver being configured to receive an expander adapted to expand a tooth socket within a treatment area, wherein the receiver is configured to slide between a first receiver position in which the distal end portion of the receiver is adjacent the distal end portion of the housing, and a second receiver position in which the distal end portion of the receiver is spaced from the distal end portion of the housing relative to the first receiver position, wherein a larger part of the receiver extends external the housing in the second receiver position relative toward the first receiver position;

an actuator disposed within the housing and configured to slide the receiver from the first receiver position toward the second receiver position, wherein the actuator includes a biasing member and a plunger configured to slide from a first position in which the plunger is retracted and spaced from the proximal end portion of the receiver, to a second position in which the plunger contacts the proximal end portion of the receiver when the receiver is in the first receiver position, and to a third position in which the plunger is fully extended and slides the receiver from the first receiver position toward the second receiver position when the plunger contacts the proximal end portion of the receiver in the second position, the biasing member configured to return the plunger from the third position toward the first position; and a bias assembly operatively connected to the receiver and configured to urge the receiver towards the second receiver position when the plunger is in at least the first position and when the actuator is configured to slide the receiver from the first receiver position toward the second receiver position, wherein the receiver is configured to be slid from the second receiver position toward the first receiver position by pushing the expander against the treatment area against urging from the bias assembly, and wherein the actuator is configured to slide the receiver from the first receiver position toward the second receiver position independent of the bias assembly, and the bias assembly is configured to urge the receiver toward the second receiver position independent of the actuator, wherein the bias assembly is spaced from the biasing member and is positioned external the receiver and the housing.

* * * * *